(12) United States Patent
Hoffmann

(10) Patent No.: US 9,511,008 B2
(45) Date of Patent: Dec. 6, 2016

(54) CONDITIONING COMPOSITION FOR KERATIN FIBRES AND ITS USE

(75) Inventor: Martin Hoffmann, Zwingenberg (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 13/638,293

(22) PCT Filed: Apr. 19, 2011

(86) PCT No.: PCT/EP2011/056262
§ 371 (c)(1),
(2), (4) Date: Sep. 28, 2012

(87) PCT Pub. No.: WO2011/131687
PCT Pub. Date: Oct. 27, 2011

(65) Prior Publication Data
US 2013/0032165 A1    Feb. 7, 2013

(30) Foreign Application Priority Data
Apr. 23, 2010    (EP) .................................... 10004330

(51) Int. Cl.
| | | |
|---|---|---|
| *A61Q 5/12* | (2006.01) | |
| *A61K 8/41* | (2006.01) | |
| *A61K 8/37* | (2006.01) | |
| *A61K 8/891* | (2006.01) | |
| *A61Q 5/02* | (2006.01) | |

(52) U.S. Cl.
CPC . *A61K 8/41* (2013.01); *A61K 8/37* (2013.01); *A61K 8/891* (2013.01); *A61Q 5/02* (2013.01); *A61Q 5/12* (2013.01); *A61K 2800/88* (2013.01)

(58) Field of Classification Search
None
See application file for complete search history.

(56) References Cited

U.S. PATENT DOCUMENTS

| | | | |
|---|---|---|---|
| 3,927,199 A | 12/1975 | Micchelli et al. | |
| 2005/0069517 A1* | 3/2005 | Lim .......... | A61Q 5/12 424/74 |
| 2007/0110694 A1* | 5/2007 | Hoffmann ............... | A61K 8/37 424/70.12 |
| 2007/0110695 A1* | 5/2007 | Hoffmann et al. ........ | 424/70.12 |
| 2007/0166272 A1* | 7/2007 | Kaharu ................... | 424/70.122 |

FOREIGN PATENT DOCUMENTS

| | | |
|---|---|---|
| EP | 0070074 A2 | 1/1983 |
| EP | 0358216 A2 | 3/1990 |
| EP | 0524612 A2 | 1/1993 |
| EP | 0640643 A2 | 3/1995 |
| EP | 1 219 290 A2 | 7/2002 |
| EP | 1 283 030 A1 | 2/2003 |
| EP | 1 493 424 A1 | 1/2005 |
| EP | 1 894 556 A2 | 3/2008 |
| EP | 2 161 016 A1 | 3/2010 |
| WO | WO 2009/059455 | * 5/2009 |

OTHER PUBLICATIONS

International Search Report Dated May 17, 2011, Mailed May 24, 2011.

* cited by examiner

*Primary Examiner* — Jyothsna Venkat
(74) *Attorney, Agent, or Firm* — Norris McLaughlin & Marcus PA

(57) ABSTRACT

The present invention is related to an aqueous conditioning composition for hair comprising at least one alkyl ether alkyl amine or alkyl ether alkyl quaternary amine and at least one compound selected from fatty acid fatty alcohol esters and arylated silicones.

4 Claims, No Drawings

CONDITIONING COMPOSITION FOR KERATIN FIBRES AND ITS USE

This application is a 371 application of PCT/EP2011/056262 filed Apr. 19, 2011, which claims foreign priority benefit under 35 U.S.C. §119 of European Application No. 10004330.6 filed Apr. 23, 2010.

The present invention is related to an aqueous conditioning composition for hair comprising at least one alkyl ether alkyl amine or alkyl ether alkyl quaternary amine and at least one compound selected from fatty acid fatty alcohol esters and arylated silicones. Present invention is also related to the use of at least one alkyl ether alkyl amine or alkyl ether alkyl quaternary amine compound for hydrophobizing surface of keratin fibers, especially human hair and especially damaged keratin fibers surfaces. Conditioning composition of the present invention can be in the form of a shampoo, cleansing—conditioning composition, or in the form of a conditioner used after washing hair with cleansing compositions.

Conditioning compositions for hair have been known for ages. Various types of conditioners are available on the market and new ones are being introduced almost every day. Despite this extremely developed conditioner market, there is still need for improvements.

Additionally, from number of patent or non-patent literature, it has generally been known to use quaternary ammonium compounds, amine compounds, silicone compounds of various chemical natures and fatty acid fatty alcohol esters in hair conditioning compositions.

Consumers with damaged hair often are not satisfied with hair conditioning effect of known conditioners because in case they chose a rich conditioner the hair afterwards does not have any volume and/or body and after a lighter conditioner use, hair is not conditioned enough so that it is not combable, does not appear shiny, it is not manageable, etc. In other words for consumers with damaged hair which is not homogeneous in degree of damage, it is very hard to find a correct conditioner. Therefore, there is a great need for a conditioner which homogeneously conditions damaged and healthy hair.

It is well known that healthy hair surface has certain natural hydrophobicity which prevents healthy hair to take up unnecessary moisture from environment and it forms a kind of protective layer that the damaging influences from the environment can reach hair inside more difficult. In other words, natural hydrophobicity of hair surface is a protective layer which protects hair from environmental damaging effects similar to a protection shield.

In hairdressing area, it is also well known that especially oxidative and reductive treatments to hair cause hair damage and damage is at highest level at the surface. Such hair is more sensitive to damaging effects from the environment and especially takes up more moisture.

The objective of the current invention is to provide conditioning compositions for hair which provides hair surface its natural hydrophobicity and conditions damaged and healthy hair homogeneously, so that hair is combable, and other properties of hair are maintained or also improved such as shine, elasticity, volume, body and manageability.

It has surprisingly been found out that a composition comprising at least one alkyl ether alkyl amine or alkyl ether alkyl quaternary ammonium compound and at least one compound selected from fatty acid fatty alcohol esters and arylated silicone provides hair surface, especially damaged hair surface, its natural hydrophobicity and conditions damaged and healthy hair excellently homogeneously so that hair becomes combabale, has shine, elasticity, volume, body and manageable.

Furthermore, it has surprisingly found out that a compositions comprising at least one alkyl ether alkyl amine or alkyl ether alkyl quaternary ammonium compound provides hair surface especially damaged hair surface its natural hydrophobicity.

Accordingly, the first object of the present invention is the use of a composition comprising at least one compound according to general structure

wherein $R_1$ is a saturated or unsaturated, straight or branched alkyl group with 8 to 24 C atoms, $R_2$ is a straight or branched alkyl group with 1 to 4 C atoms which may be substituted, A is O and B is selected from

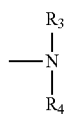

wherein $R_3$ and $R_4$ are the same or different, H or an alkyl with 1 to 4 C atoms, hydroxyl alkyl with 1 to 4 C atoms and di hydroxyl alkyl with 2 to 4 C atoms and

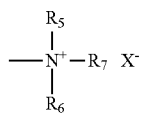

$R_5$, $R_6$ and $R_7$ are the same or different, an alkyl with 1 to 4 C atoms, hydroxyl alkyl with 1 to 4 C atoms and di hydroxyl alkyl with 2 to 4 C atoms, and X is an anion such as chloride, bromide, methosulfate, for hydrophobizing and conditioning keratin fibres, especially human hair, especially damaged human hair.

Further object of the present invention is that a conditioning composition comprising at least one compound according to general structure

wherein $R_1$ is a saturated or unsaturated, straight or branched alkyl group with 8 to 24 C atoms, $R_2$ is a straight or branched alkyl group with 1 to 4 C atoms which may be substituted, A is O and B is selected from

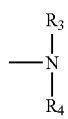

wherein $R_3$ and $R_4$ are the same or different, H or an alkyl with 1 to 4 C atoms, hydroxyl alkyl with 1 to 4 C atoms and di hydroxyl alkyl with 2 to 4 C atoms and

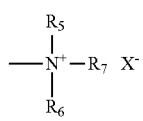

$R_5$, $R_6$ and $R_7$ are the same or different, an alkyl with 1 to 4 C atoms, hydroxyl alkyl with 1 to 4 C atoms and di hydroxyl alkyl with 2 to 4 C atoms, and X is an anion such as chloride, bromide, methosulfate, and at least one compound selected from fatty acid fatty alcohol ester according to general structure $$R_{40}C(O)OR_{41}$$

wherein $R_{40}$ is a saturated or unsaturated, straight or branched alkyl group with 7 to 23 C atoms and $R_{41}$ is a saturated or unsaturated, straight or branched alkyl group with 8 to 24 C atoms and arylated silicone.

Still further object of the present invention is the use of the above composition for conditioning and hydrophobizing keratin fibres, especially human hair and in particular damaged hair.

Still further object of the present invention is the method of conditioning hair wherein hair is treated with at least one composition as mentioned above and optionally rinsed off from hair after a processing time of up to 30 min.

Compositions of the present invention are suitable for either rinse off or leave in applications. Further object of the present invention is process for conditioning hair wherein a composition according to present invention is applied onto hair and not rinsed off.

The compositions of the present invention can be either a conditioning—cleansing composition—shampoo—or a conditioning composition typically used after use of cleansing compositions.

Compositions of the present invention comprise at least one alkyl ether alkyl amine or alkyl ether alkyl quaternary amine compound according to the above general structure. In the preferred embodiment of the present invention, $R_1$ is saturated or unsaturated, straight or branched alkyl group with 10 to 24 C atoms, more preferably 12 to 22 C atoms and $R_2$ is straight or branched alkyl group with 1 to 4 C atoms which may be substituted and preferably ethyl or hydroxyl ethyl, A, B, $R_3$ to $R_7$ are same as above. Non-limiting suitable examples are stearoxypropyl amine, palmitoxypropyl amine, stearoxypropyldimethyl amine, stearoxypropyldiethyl amine, stearoxyethylyldimethyl amine, stearoxyethyl amine, myristoxypropyl amine, myristoxypropyldimethyl amine, stearoxypropyl trimethyl ammonium chloride, palmitoxypropyl trimethyl ammonium chloride, stearoxypropyl trimethyl ammonium chloride, stearoxypropyltriethyl ammonium chloride, stearoxyethylyltrimethyl ammonium chloride, stearoxyethyl trimethyl ammonium chloride, myristoxypropyl trimethyl ammonium chloride and myristoxypropyltrimethyl ammonium chloride. Preferred are the ones with palmit and stear derived alkyl groups and most preferred are the ones with stear group such as stearoxypropyldimethyl amine.

Concentration of at least one alkyl ether alkyl amine or alkyl ether alkyl quaternary amine according to the above general structure is in the range of 0.01 to 20%, preferably 0.02 to 15%, more preferably 0.05 to 10% and most preferably 0.1 to 7.5% and in particular 0.25 to 5% by weight calculated to total composition.

Compositions of the present invention comprise at least one arylated silicone and/or at least one fatty acid fatty alcohol ester. Non-limiting suitable arylated silicones are phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane.

Non-limiting suitable examples to fatty acid fatty alcohol esters are isopropyl myristate, palmitate, stearate and isostearate, oleyl oleate, isocetyl stearate, hexyl laurate, dibutyl adipate, dioctyl adipate, myristyl myristate and oleyl erucate.

Composition of the present invention comprises at least one arylated silicone and/or at least one fatty acid fatty alcohol ester at a concentration of 0.01 to 10%, preferably 0.02 to 7.5%, more preferably 0.05 to 5% and most preferably 0.1 to 3% by weight calculated to total composition.

The composition of the present invention can comprise additionally other hair-conditioning agents in any type of composition. Conditioning agents can be selected from oily substances, non-ionic substances, other cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, natural oils such as olive oil, almond oil, avocado oil, wheatgerm oil, ricinus oil and the synthetic oils, such as mineral oil.

Concentration of one or more oily substances which may be present in addition to the arylated silicones and fatty acid fatty alcohol esters is in the range of 0.01 to 10%, preferably 0.05 to 7.5%, more preferably 0.1 to 5 and most preferably 0.1 to 3% by weight calculated to total composition. The concentrations referred here are total concentration of all oily substances may be present in the composition.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_8CO(OCH_2CH_2)_nOH \text{ or}$$

$$R_8CO(OCH_2CH_2)_nOOCR_9$$

where $R_8$ and $R_9$ are independent from each other saturated, unsaturated or branched or non-branched alkyl chain with 7 to 21 C atoms and n is typically 2-100.

In one of the preferred from of the present invention, conditioning compositions comprise at least one cationic polymer as conditioning agent. Suitable cationic polymers are those of best known with their INCI category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87 as well as silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20, silicone quaternium-21 and silicone quaternium-22.

As well those polymers known with their INCI category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from RhOne-Poulenc which are chemically for example Guar hydroxypropyl trimonium chloride and cationic tara gum an its derivatives known with INCI name *Caesalpinia spinosa* hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic *Caesalpinia spinosa* gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Conditioning compositions of the present invention can comprise additionally one or more cationic surfactant(s) as conditioner presented with the general formula

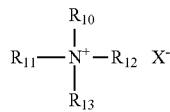

where $R_{10}$ is a saturated or unsaturated, branched or non-branched alkyl chain with 8-24 C atoms and $R_{11}$ is unsaturated or saturated, branched or non-branched alkyl chain with 1-24 C atoms and $R_{12}$ and $R_{13}$ are lower alkyl chain with 1 to 4 carbon atoms which may be substituted with one or more hydroxyl groups, and X is anion such as chloride, bromide, methosulfate.

Typical examples of those ingredients are cetyltrimethyl ammonium chloride, steartrimonium chloride, behentrimonium chloride, myristyltrimethyl ammonium chloride, distearyldimethyl ammonium chloride, and dibehenyldimethyl ammonium chloride. The others known in the textbooks are included herewith by reference.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, and cationic surfactants can be 0.01-10% by weight, preferably 0.01-7.5% by weight, more preferably 0.05-5% and most preferably 0.1-3% by weight calculated to the total composition. It should be noted that especially non-cleansing conditioning type of the products contain higher concentrations of the above mentioned concentrations of the cationic surfactants which at the same time if desired can be emulsifying agent. In cleansing and conditioning type of preparations, concentration of cationic surfactants is lower.

Composition of the present invention can preferably comprise at least one polyphenol. With the word polyphenol it is meant that an organic molecule with at least 2 hydroxyl groups in its molecule.

In the preferred from of the invention, at least one polyphenol or mixture of polyhenols is included into compositions of the present invention from a natural plant extract. In principal any natural plant extract rich of polyphenols is suitable within the meaning of the present invention. Within the meaning of the present invention the extracts are liquid extracts and prepared by mixing plant parts such as leaves, fruits, blossoms and roots with a solvent such as water, alcohol, propyleneglycol or mixture of more than one solvent and incubating for certain period of time and filtrating the undissolved plant parts. Suitable aqueous (e.g. steam-distilled) alcoholic or hydro-alcoholic plant extracts known per se are in particular aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", 4$^{th}$ Ed. Preferred plant extracts are prepared from *Vitis vinifera, Malus domestica, Camelia sinensis, Juglans regia Ribes Uva-Crispa, Ribes nigrum, Ribes rubrum* and *Punica granatum*. The above mentioned extracts may also be available in the powder form and such are also suitable within the meaning of the present invention.

The polyphenol comprising extracts are included into the compositions of the present invention at a concentration of 0.001 to 10%, preferably 0.005 to 7.5%, more preferably 0.01 to 5% and most preferably 0.05 to 2.5% by weight, calculated to total composition based on dry matter of the extract.

Further in preferred embodiment of the present invention, compositions comprise at least one UV filter and at least one ubichinone of the following formula

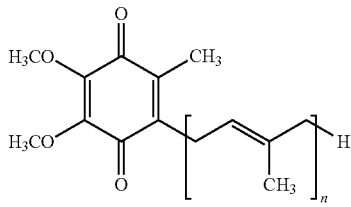

where n is a number between 1 and 10. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Compositions of the present invention preferably comprise at least one UV filter. Principally any substance known as UV filter is suitable for the compositions of the present invention. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecamphor, 3-(4'-sulfo)-benzyl-idenebornane-2-one and the salts thereof, 3-(4'-methyl benzylidene)-DL-campher, and/or polysilicone-15. Above mentioned UV filters are those oil and water soluble ones for the purpose of protecting hair colour. In other words, anionic and nonionic, oily, UV filters are suitably used in the compositions of the present invention. In the preferred from of the invention the compositions comprise at least one water soluble UV filter and at least one oil soluble one. Further preferred that both UV filters are present at a weight ratio in the range of oil soluble to water soluble UV filter 1:10 to 10:1, preferably 1:5 to 5:1, more preferably 1:3 to 3:1 and most preferably 1:1 in the compositions of the present invention.

The amount of the UV-absorber as a total ranges typically from about 0.01% to 5%, preferably 0.05 to 3%, more preferably from 0.05% to 2.5% and most preferably from 0.1% to 2% by weight, calculated to the total composition.

In another preferred form of the invention, conditioning composition can comprise one or more organic solvent such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzylalcohol and polypropylene glycols. Concentration of organic solvents should not exceed 10% by weight, preferably in the range of 0.1 to 7.5%, more preferably 0.1 to 5% by weight and most preferably 0.1 to 3% by weight calculated to total composition.

Conditioning composition of the present invention comprises at least one glyceryl ether of the following formula

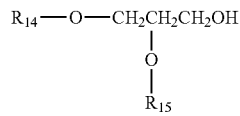

wherein $R_{14}$ is straight or branched, saturated or unsaturated alkyl chain with 4 to 24 C atoms, preferably 4 to 18 and more preferably 4 to 12 C atoms and $R_{15}$ is H, or straight or branched, saturated or unsaturated alkyl chain with 4 to 24 C atoms, preferably 4 to 18 and more preferably 4 to 12 C atoms and most preferably $R_5$ is H, at a concentration of 0.1 to 10%, preferably 0.1 to 5% and more preferably 0.25 to 3% and most preferably 0.5 to 2.5% by weight calculated to total composition.

Suitable unlimited examples are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Most preferred are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether are glyceryl lauryl ether, and their mixtures.

It should be noted that within the disclosure of the present description, gylceryl decyl ether is used as synonym of decyl glycerine. For the other compounds in the above paragraph the same is valid.

Further in preferred embodiment of the present invention, compositions comprise at least one direct dye. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuffs is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

Conditioning compositions of the present invention can be a cleansing composition (cleansing-conditioning composition). Cleansing conditioning compositions of the present invention comprise at least one surfactant selected from anionic, non-ionic and/or amphoteric or zwitterionic surfactants at a concentration range of 5 to 50%, preferably 5 to 40% and more preferably 5 to 30%, and most preferably 5 to 25% by weight, calculated to the total composition.

In an embodiment of the present invention, cleansing conditioning composition of the present invention comprises at least one anionic, at least one nonionic surfactant. More preferably the compositions further comprise additionally at least one amphoteric surfactant.

Anionic surfactants suitable within the scope of the invention are preferably present in an amount from 1 to about 30%, preferably 2 to 20% and most preferably 2-15%, by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether)sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

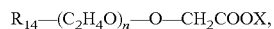

$R_{14}$—$(C_2H_4O)_n$—O—$CH_2COOX$, wherein $R_{14}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

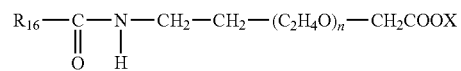

$$R_{16}-\underset{\underset{O}{\|}}{C}-\underset{\underset{H}{|}}{N}-CH_2-CH_2-(C_2H_4O)_n-CH_2COOX$$

wherein $R_{16}$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

An overview of the anionic surfactants used in liquid body cleansing compositions can furthermore be found in the monography of K. Schrader and A. Domsch, "Cosmetology—Theory and Practice", 2005, Verlag für chemische Industrie, Augsburg-Germany, pp. II-8-II-19.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Further surfactants in the conditioning—cleansing compositions according to the invention are nonionic surfactants, preferably in admixture with anionic surfactants.

These are described in Schrader, l.c., on pages 600-601 and pp. 694-695. Especially suited are alkyl polyglucosides of the general formula

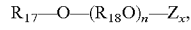

$R_{17}$—O—$(R_{18}O)_n$—$Z_x$, wherein $R_{17}$ is an alkyl group with 8 to 18 carbon atoms, $R_{18}$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides which may be present in an amount from 0.25% to 5% by weight, calculated to the total composition.

Such amineoxides are state of the art, for example $C_{12}$-$C_{18}$-alkyl dimethyl aminoxides such as lauryl dimethyl aminoxide, $C_{12}$-$C_{18}$-alkyl amidopropyl or -ethyl aminoxides, $C_{12}$-$C_{18}$-alkyl di(hydroxyethyl) or (hydroxypropyl) aminoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the cleansing conditioning compositions according to invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the cleansing conditioning compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

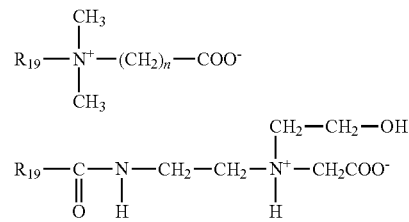

wherein $R_{19}$ is a $C_8$-$C_{18}$-alkyl group and n is 1 to 3; sulfobetaines of the structure

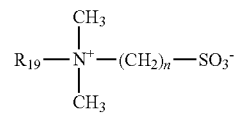

wherein $R_{19}$ and n are same as above; and amidoalkyl betaines of the structure

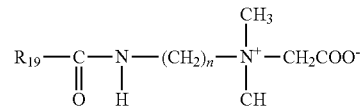

wherein $R_{19}$ and n are same as above.

Solubilizers may be added to the compositions, in particular cleansing compositions, especially when oily substances are chosen as conditioning agents and fragrance oils with highly lipophilic properties. Typical solubilizers may be hydrogenated castor oil known with the trade mark Cremophor RO series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

Further conditioning additives are hair conditioning and/or styling polymers into either cleansing or conditioning type. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning composition of any type of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryloylethyl betaine and alkyl-methacrylates of the type "Yukaformer®", e.g., the butyl methacrylate copolymer "Yukaformer®

Am75"; copolymers from monomers containing carboxyl groups and sulfonic groups, e.g., (meth)acrylic acid and itaconic acid, with monomers such as mono- or dialkyl amino alkyl(meth)acrylates or mono- or dialkyl-aminoalkyl (meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199, are applicable.

Conditioning and cleansing composition of the present invention can be transparent as well as pearly. Transparency of the composition is judged by naked eye in a transparent shampoo bottle with a thickness not more than 5 cm. In the case a transparent appearance is wished, the following ingredients are not essential. However, pearl-shiny appearance is achieved with those dispersed in cleansing color-enhancing compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kind of mixtures is available commercially.

Hair cleansing conditioning compositions of the present invention can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbondioxide, dimethylether and alkanes such as butane propane or their mixtures.

Conditioning compositions of the present invention can be in the form of emulsions, solutions, gels and dispersions. In the case that solutions and/or gels forms are preferred the appearance can be either with a transparent or opaque.

As a product form, foam is as well suited when packed into a pressurized can or delivered through a pump-foamer (non-aerosol). In the case that an aerosol foam preparation is preferred, propellant gas must be added to the formulation. The suitable propellant gasses are carbondioxide, dimethylether and alkanes such as butane, propane, isobutane or their mixtures.

The emulsion type of conditioning compositions comprise additionally at least one fatty alcohol of the following formula

$R_{30}$—OH where $R_{30}$ is a saturated or unsaturated, branched or non-branched fatty acyl chain with 8-24 C atoms. Concentration of fatty alcohols is usually less than 20%, preferably less than 15% by weight calculated to total composition. Typical examples to the most useful fatty alcohols are myristyl alcohol, palmityl alcohol, cetyl alcohol, stearyl alcohol, behenyl alcohol and their mixtures. As a mixed fatty alcohol the mostly used one is the cetearyl alcohol as well preferred in the compositions of the present invention.

Conditioning compositions of the present invention can comprise moisturizers, chelating agents, preservatives and fragrance. The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The pH of the compositions according to the present invention is suitably between 1.5 and 8 and preferably in the range of 2 to 7, more preferably 2.5 to 6.5 and most preferably 3 to 6.

In principal pH of the compositions can be adjusted with any organic and/or inorganic acids or their mixture. Some of them to mention are phosphoric acid, hydrochloric acid as the inorganic ones and to the organic acids the well known citric acid and lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. It has further been observed that improved conditioning and brightening performance was observed when compositions comprise at the same time at least one hydroxycarboxylic and/or dicarboxylic acids.

The viscosity of the conditioning shampoo compositions according to the invention is in the range of 500 and about 20,000 mPa·s at 20° C., preferably 1,000 to 10,000, in particular 1,500 to 8,000 mPa·s at 20° C., measured with Höppler viscosimeter.

Viscosity of shampoo compositions can be adjusted with known viscosity enhancers. The preferred ones are glyceryl laurate, PEG-55 propyleneglycol oleate and PEG-18 glyceryl oleate/cocoate known with the trade names Antil® 141 and 171, respectively, PEG-160 sorbitan triisostearate known with a trade name Rheodol® and sorbitan esters such as sorbitan sesquicaprylate known with trade name Antil Soft SC. It should be noted that in the case that a composition are delivered in the form of a foam from a pump-foamer and/or aerosol can, those compositions should not be thickened and have a viscosity value not more than 500 mPa·s, more preferably 250 mPa·s measured as mentioned above at room temperature.

Viscosity of the non-cleansing conditioning composition may not be more than 50,000 mPa·s at 20° C. measured with Brookfield Rheometer at a shear rate of 10 sec$^{-1}$.

It has been observed that conditioning and hydrophobizing effects are at optimum when one of the cleansing and conditioning compositions, preferably both compositions comprises at least one alkyl ether alkyl amine or alkyl ether alkyl quaternary ammonium compound. Therefore, another object of the present invention is a kit for conditioning hair which comprise more than one hair conditioning composition, preferably two to three compositions, more preferably two composition, wherein at least one of the compositions, preferably two compositions more preferably all compositions comprise at least one alkyl ether alkyl amine or alkyl ether alkyl quaternary ammonium of the above given structure.

The following examples are to illustrate the invention, but not to limit. The compositions according to the invention are prepared by mixing the individual components in water, whereby it is also possible to use pre-mixtures of various ingredients.

EXAMPLE 1

| | % by weight |
|---|---|
| Stearoxypropyldimethyl amine | 1.0 |
| Citric acid | q.s. pH 4.0 |
| Ethanol | 10 |
| Fragrance, preservative | q.s. |
| Water | to 100 |

The above composition was prepared by dissolving stearoxypropyl dimethyl amine in water at approximately 50° C. and adjusting the pH to 4.0. After cooling down the remaining ingredients were added.

The composition improves hydrophobicity of the hair surface which was visualized by determining the disappearing time of a water droplet comprising a blue dyestuff (CI 42090) at a concentration of 0.0001% by weight in water at ambient temperature such as 20° C. The longer the disappearing time, the higher the hydrophobicity of the hair surface. It was observed that the droplet disappearing time was much longer on hair treated with the above composition, 0.2 g per g hair of the above composition was applied and without rinsing of hair was dried, than the one treated with the same composition without stearoxypropyl dimethyl amine. This shows very clearly the hydrophobizing effect of the above composition comprising stearyloxypropyl amine.

EXAMPLE 2

| | % by weight |
|---|---|
| Stearoxypropyl dimethyl amine | 1.0 |
| Phenyl trimethicone | 1.0 |
| Cetearyl alcohol | 7 |
| Cetrimonium chloride | 1.5 |
| Citric acid | q.s. pH 4.0 |
| Fragrance, preservative | q.s. |
| Water | to 100 |

The above composition was prepared by disolving Stearoxypropyl dimethyl amine in water at around 50° C. and adjusting pH to 4.0 and emulsifiying after adding fatty alcohol and cetrimonium chloride at around 70° C. and after cooling down to 40° C. phenyl trimethicone was added to the emulsion and the other components of the composition are added subsequently.

The composition conditions hair with parts damaged in various degrees homogeneously so that hair is combabale, has shine, elasticity, volume and it is manageable. Additionally it was observed that hydrophobicity of the damaged parts as determined with the method described under example 1 was similar to the parts of natural, non damaged hair.

EXAMPLE 3

| | % by weight |
|---|---|
| Stearoxypropyl dimethyl amine | 1.0 |
| Isopropylmyristate | 1.5 |
| Behenyl alcohol | 5 |
| Ceteareth-20 | 2 |
| Polyquaternium-10 | 1 |
| Lactic acid | q.s. pH 4.2 |
| Fragrance, preservative | q.s. |
| Water | to 100 |

EXAMPLE 4

| | % by weight |
|---|---|
| Stearoxypropyl dimethyl amine | 0.5 |
| Pentaphenyl trimethyl siloxane | 0.5 |
| Isopropyl myristate | 0.5 |
| Polyquaternium-6 | 1 |
| Lactic acid | q.s. pH 5.0 |
| Fragrance, preservative | q.s. |
| Water | to 100 |

The above composition was used as a leave-in conditioner from a pump spray bottle on damaged hair which was freshly washed and towel dried. In dry state it was observed that hair was easily combable, had elasticity, volume and body. Increased hydrophobicity was also observed.

EXAMPLE 5

| | |
|---|---|
| Stearoxypropyl dimethyl amine | 0.5% by weight |
| Phenyl trimethicone | 0.5% |
| Myristyl myristate | 1 |
| Lactic acid | q.s. pH 5.0 |
| Fragrance, preservative | q.s. |
| Water | to 100 |

The above composition was used as a leave-in conditioner from a pump spray bottle on damaged hair which was freshly washed and towel dried. In dry state it was observed that hair was easily combable, had elasticity, volume and body. Increased hydrophobicity was also observed.

EXAMPLE 6

| | % by weight |
|---|---|
| Stearoxypropyl dimethyl amine | 0.5% |
| Dioleoylethylhydroxyethylmonium methosulfate | 1 |
| Silicone Quaternium-22 | 0.5 |
| DC HMW 2220 | 1 |
| Cetearyl alcohol | 7 |
| Ceteareth-20 | 3 |
| Benzophenone-3 | 0.4 |
| Panthenol | 0.5 |
| Phenyl trimethicone | 0.3 |
| Citric acid | q.s. pH 4.0 |
| Fragrance, preservative | q.s. |
| Water | to 100 |

The above composition was especially suitable for coloured and/or highlighted hair. The coloured hair treated with the above conditioner is exceptionally shiny, well combable and has elasticity, volume and body. Increased hydrophobicity was also observed.

EXAMPLE 7

|  | % by weight |
| --- | --- |
| Stearoxypropyl dimethyl amine | 1 |
| Silicone Quaternium-18 | 1 |
| Palmityl palmitate | 0.1 |
| Cetearyl alcohol | 7 |
| Ceteareth-20 | 3 |
| Benzophenone-3 | 0.4 |
| Panthenol | 0.5 |
| Diphenyl dimethicone | 0.3 |
| Citric acid | q.s. pH 4.0 |
| Fragrance, preservative | q.s. |
| Water | to 100 |

The above composition was especially suitable for coloured and/or highlighted hair. The coloured hair treated with the above conditioner is exceptionally shiny, well combable and has elasticity, volume and body. Increased hydrophobicity was also observed.

EXAMPLE 8

|  | % by weight |
| --- | --- |
| Stearoxypropyl dimethyl amine | 2.5 |
| Cetearyl alcohol | 7 |
| Ceteareth-20 | 3 |
| Isopropyl palmitate | 0.2 |
| Benzophenone-3 | 0.4 |
| Glycerin | 3 |
| Trimethyl pentaphenyl trisiloxane | 0.3 |
| Basic red 51 | 0.1 |
| Citric acid | q.s. pH 4.2 |
| Fragrance, preservative | q.s. |
| Water | to 100 |

Above conditioner gives dark blonde hair red shimmer and shows excellent hydrophobizing effect.

EXAMPLE 9

|  | % by weight |
| --- | --- |
| Stearoxypropyl dimethyl amine | 1.5 |
| Silicone Quaternium-18 | 1 |
| Cetearyl alcohol | 7 |
| Ceteareth-20 | 3 |
| Ethyl hexyl methoxy cinnamate | 0.4 |
| Glycerin | 3 |
| Trimethyl pentaphenyl trisiloxane | 0.3 |
| Cetyl palmitate | 0.2 |
| Basic red 51 | 0.01 |
| Basic yellow 87 | 0.1 |
| Basic brown 16 | 0.02 |
| Citric acid | q.s. pH 4.2 |
| Fragrance, preservative | q.s. |
| Water | to 100 |

Above conditioner gives light blonde hair additional blond shine and shows excellent hydrophobizing effect.

EXAMPLE 10

|  | % by weight |
| --- | --- |
| Stearoxypropyl dimethyl amine | 1 |
| Silicone Quaternium-22 | 1 |
| Cetearyl alcohol | 7 |
| Ceteareth-20 | 3 |
| Isopropyl palmitate | 0.1 |
| Polysilicone-15 | 0.4 |
| Glycerin | 3 |
| Phenyl trimethicone | 0.3 |
| Coenzyme Q10 | 0.08 |
| Ethyl hexyl glycerin | 0.5 |
| Citric acid | q.s. pH 4.2 |
| Fragrance, preservative | q.s. |
| Water | to 100 |

Above conditioner enhances combability, shine, volume body and elasticity. Hair treated with the above conditioner is excellently manageable and easily styled together with increased hydrophobicity of hair surface.

EXAMPLE 11

|  | % by weight |
| --- | --- |
| Stearoxypropyl dimethyl amine | 1 |
| Silicone Quaternium-22 | 1 |
| Cetearyl alcohol | 7 |
| Steartrimonium chloride | 1 |
| Glycerin | 3 |
| Phenyl trimethicone | 0.3 |
| Coenzyme Q10 | 0.08 |
| Isopropyl myristate | 0.2 |
| Lactic acid | q.s. pH 3.8 |
| Fragrance, preservative | q.s. |
| Water | to 100 |

Above conditioner enhances combability, shine, volume body and elasticity. Hair treated with the above conditioner is excellently manageable and easily styled. Above conditioner was also used as leave in conditioner and bodyfying effects was especially enhanced together with increased hydrophobicity of hair surface.

EXAMPLE 12

|  | % by weight |
| --- | --- |
| Stearoxypropyl dimethyl amine | 1 |
| Silicone Quaternium-22 | 1 |
| Cocamidoproyl betaine | 0.8 |
| Steartrimonium chloride | 1 |
| Glycerin | 3 |
| Coenzyme Q10 | 0.08 |
| Pentaphenyl trimethyl siloxane | 0.1 |
| Isopropyl myristate | 0.1 |
| Lactic acid | q.s. pH 3.8 |
| Fragrance, preservative | q.s. |
| Water | to 100 |

Above composition had a viscosity below 500 mPa·s and was filled into a pump foamer and used as leave in conditioner on a freshly washed and towel dried hair. Hair was excellently shiny and bodified also excellently combable. Additionally hydrophobized hair surface was determined with the method described under example 1.

The above composition was also used as aerosol foam and therefore filled into an aerosol can with 10% propane-butane mixture as a propellant. The above results were confirmed. The above composition can also be used as a pump spray.

EXAMPLE 13

| | |
|---|---|
| Cetylstearylalcohol | 5.0 (% by weight) |
| Stearoxypropyl dimethylamine | 1.0 |
| Ceteareth 20 | 1.0 |
| Silicone Quaternium-22 | 0.2 |
| Isopropyl palmitate | 0.1 |
| DC HMW 2220 | 0.55 |
| Hydroxypropyl Guar Hydroxypropyltrimonium Chloride | 1.0 |
| Ethylhexyl glycerin | 0.8 |
| Tetramethyl tetraphenyl trisiloxane | 0.2 |
| *Ribes nigrum* (dry matter) | 0.1 |
| Avocado extract | 0.5 |
| Fragrance, preservative | q.s. |
| Malic acid | q.s. to pH 3.5 |
| Wasser | ad 100.0 |

EXAMPLE 14

| | |
|---|---|
| Cetylstearylalcohol | 5.0 (% by weight) |
| Stearyltrimethylammoniumchlorid | 1.0 |
| Silicone Quaternium-22 | 1.2 |
| Stearoxypropyldimethyl amine | 1.0 |
| Benzylalcohol | 2.5 |
| Trimethyl pentaphenyl trisiloxane | 0.3 |
| Ethylhexyl glycerin | 0.9 |
| Fragrance, preservative | q.s. |
| Lactic acid | q.s. pH 3.5 |
| Wasser | ad 100.0 |

Above composition is applied onto shampooed hair and processed for 5 min and rinsed off from hair. It was observed that wet hair is easily combable. In the dry state combability, manageability, elasticity and shine were very much improved in addition to the hydrophobizing effect of the hair surface.

Furthermore into the above conditioner composition, hair direct dye Basic red 51 was included. After use on dark blonde hair am excellent red shine was observed on the hair.

EXAMPLE 15

| Foam conditioner | |
|---|---|
| Stearoxypropyl dimethyl amine | 0.5 (Gew.-%) |
| Polyquaternium-11 | 0.7 |
| PEG-60-hydrogenated *ricinus* oil | 0.5 |
| Diphenylsiloxy phenyl trimethicone | 0.5 |
| Ethylhexyl glycerin | 1.2 |
| Silicone Quaternium-22 | 0.2 |
| Stearamidopropyldimethyl amine | 1.0 |
| *Malus domestica* (dry matter) | 0.1 |
| Ubichinone | 0.075 |
| Benzophenone-3 | 0.3 |
| Fragrance, preservative | q.s. |
| Lactic acid | q.s. to pH 3.4 |
| Wasser | ad 100.0 | pH of the composition is adjusted to 3.4. The composition is suitable for leave-in and rinse off. In leave-in application, amount used is obviously less than in the case of a rinse of application. The composition is packed into an aerosol can with 90/10 ratio, by weight, liquid composition to propellant. As propellant propane, butane mixture is used.

Into the above composition 0.1% Acid red 52 was added. It was possible to realize red shimmer onto dark blonde hair. Improved hydrophobicity was observed both in leave-in and rinse off applications.

EXAMPLE 16

| Foam conditioner | |
|---|---|
| Quaternium-80 | 0.2 (Gew.-%) |
| Polyquaternium-11 | 0.7 |
| PEG-60-hydrogenated *ricinus* oil | 0.5 |
| Diphenylsiloxy phenyl trimethicone | 0.5 |
| Ethylhexyl glycerin | 1.2 |
| Silicone Quaternium-22 | 0.2 |
| Stearoxypropyldimethyl amine | 1.0 |
| Isopropyl palmitate | 0.1 |
| Ubichinone | 0.075 |
| Benzophenone-3 | 0.3 |
| Fragrance, preservative | q.s. |
| Lactic acid | q.s. to pH 3.8 |
| Wasser | ad 100.0 | pH of the composition is adjusted to 3.8. The composition is suitable for leave-in and rinse off. In leave-in application, amount used is obviously less than in the case of a rinse of application. The composition is packed into an aerosol can with 90/10 ratio, by weight, liquid composition to propellant. As propellant propane, butane mixture is used.

Into the above composition 0.1% Acid red 52 was added. It was possible to realize red shimmer onto dark blonde hair. Improved hydrophobicity was observed both in leave-in and rinse off applications.

EXAMPLE 17

| | |
|---|---|
| Cetylstearylalcohol | 5.0 (% by weight) |
| Cetrimoniumchloride | 1.0 |
| Panthenol | 0.4 |
| Silicone Quaternium-18 | 0.2 |
| Hydroxypropyl Guar Hydroxypropyltrimonium Chloride | 1.0 |
| Trimethyl pentaphenyl trisiloxane | 0.5 |
| Decyl glycerin | 1.2 |
| Stearoxypropyl diethyl amine | 1.0 |
| Ubichinone | 0.08 |
| Avocado extract | 0.5 |
| Fragrance, preservative | q.s. |
| Citric acid | q.s. to pH 3.0 |
| Wasser | ad 100.0 |

The above composition can be used as both leave-in and rinse off.

EXAMPLE 18

| | |
|---|---|
| Sodium lauryl ether sulfate | 11.0 (% by wt.) |
| Coco glucoside | 4.0 |
| Cocoamidopropyl betaine | 1.5 |
| Sodium cocyl glutamate | 1.5 |

-continued

|  |  |
|---|---|
| Silicone Quaternium-22 | 0.3 |
| Stearoxyopropyl dimethyl amine | 0.3 |
| Pentaphenly timethyl siloxane | 0.1 |
| Sodium chloride | 1.0 |
| Citric acid | q.s. pH 5.5 |
| Perfume, preservative | q.s |
| Water | q.s. to 100.0 |

Hair washed with the above shampoo composition showed excellent shine, volume, body, easily combable and improved elasticity and manageability in addition to the excellently hydrophobized surface.

EXAMPLE 19

|  | % by weight |
|---|---|
| Coco glucoside | 8.0 |
| Cocoamidopropyl betaine | 8.0 |
| Laureth-16 | 2.0 |
| Cationic polymer (Polyquaternium-11) | 0.5 |
| Benzophenone-3 | 0.2 |
| Isopropyl palmitate | 0.1 |
| Etyh hexyl glycerin | 0.8 |
| PEG-3 distearate | 0.8 |
| Coenzyme Q10 | 0.1 |
| Silicone Quaternium-18 | 0.2 |
| Stearoxyprolydihydroethylamine | 0.3 |
| PEG-18 Glyceryl cocoate/oleate | 0.80 |
| *Malus domestica* (dry matter) | 0.1 |
| Malic acid | q.s. pH 5.5 |
| Perfume, preservative | q.s. |
| Water | ad 100.0 |

To the above composition, 0.1% Basic orange 31 and 0.05% Basic red 76 was mixed. Hair washed with this shampoo had excellent warm blond shine.

EXAMPLE 20

|  |  |
|---|---|
| Sodium lauryl ether sulfate | 11.0 (% by wt.) |
| Coco glucoside | 5.0 |
| Cocoamidopropyl betaine | 3.0 |
| Sodium cocoyl gluatamate | 1.5 |
| Stearyl trimethyl ammonium chloride | 0.1 |
| Cationic polymer (Polyquaternium-11) | 0.5 |
| Benzophenone-3 | 0.2 |
| Stearoxypropyldimethylamine | 0.5 |
| Lactic acid | q.s. to pH 5.0 |
| Perfume, preservative | q.s. |
| Water | ad 100.0 |

The above composition is a very low viscosity composition, in any case a viscosity lower than 500 mPa·s measured at ambient temperature and with Höppler viscosimeter, confectioned into a pump-foamer as purchased from the company Air-Spray—Germany and showed excellent shine effect Similarly and aerosol foam shampoo was prepared by confectioning the above composition at a weight ratio of 90/10—composition/propellant—using propane-butane mixture as a propellant. The foam shampoos so obtained showed excellent cleansing and shine effects in addition to a excellent hydrophobizing effect.

Additionally, into the above shampoo 0.05% basic blue 99, and 0.005% basic red 51 was added. Excellent warm silver shine was observed on the washed gray hair. At the same time, excellent anti-yellow effect is observed on the freshly bleached hair.

Furthermore the above cleansing and conditioning composition was added 1% by weight sodium chloride and it became a thickened shampoo without loss of any effects mentioned above.

The invention claimed is:
1. A method of conditioning hair consisting of:
   applying a composition onto hair without rinsing the composition off from the hair, wherein the composition comprises
      at least one alkyl ether alkyl amine or alkyl ether alkyl quaternary amine selected from the group consisting of stearoxypropyl amine, palm itoxypropyl amine, stearoxypropyldimethyl amine, stearoxypropyldiethyl amine, stearoxyethylyldimethyl amine, stearoxyethyl amine, myristoxypropyl amine, myristoxypropyldimethyl amine, stearoxypropyl trimethyl ammonium chloride, palmitoxypropyl trimethyl ammonium chloride, stearoxypropyltriethyl ammonium chloride, stearoxyethylyltrimethyl ammonium chloride, stearoxyethyl trimethyl ammonium chloride and myristoxypropyl trimethyl ammonium chloride,
      at least fatty acid fatty alcohol ester selected from the group consisting of isopropyl myristate, isopropyl palmitate, isopropyl stearate and isopropyl isostearate, oleyl oleate, isocetyl stearate, hexyl laurate, dibutyl adipate, dioctyl adipate, myristyl myristate and oleyl erucate,
      at least one arylated silicone, and
      at least one cationic polymer selected from the group consisting of Polyquaternium-1, Polyquaternium-2, Polyquaternium-4, Polyquaternium-5, Polyquaternium-6, Polyquaternium-8, Polyquaternium-9, Polyquaternium 10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35 and Polyquaternium-36, Polyquaternium 39, Polyquaternium 42, Polyquaternium-43, Polyquaternium-45, Polyquaternium-46, Polyquaternium-47, Polyquaternium-48, Polyquaternium-49, Polyquaternium-50, Polyquaternium-51, Polyquaternium-52, Polyquaternium-53, Polyquaternium-54, Polyquaternium-55, Polyquaternium-56, Polyquaternium-57, Polyquaternium-58, Polyquaternium-59, Polyquaternium-60, Polyquaternium-61, Polyquaternium-62, Polyquaternium-63, Polyquaternium-64, Polyquaternium-65, Polyquaternium-66, Polyquaternium-67, Polyquaternium-68, Polyquaternium-69, Polyquaternium-70, Polyquaternium-71, Polyquaternium-72, Polyquaternium-73, Polyquaternium-74, Polyquaternium-75, Polyquaternium-76, Polyquaternium-77, Polyquaternium-78, Polyquaternium-79, Polyquaternium-80, Polyquaternium-81, Polyquaternium-82, Polyquaternium-83, Polyquaternium-84, Polyquaternium-85, Polyquaternium-86 and Polyquaternium-87, silicone quaternium-1, silicone quaternium-2, silicone quaternium-2 panthenol succinate, silicone quaternium-3, silicone quaternium-4, silicone quaternium-

5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20, silicone quaternium-21 and silicone quaternium-22, wherein the at least one alkyl ether alkyl amine or alkyl ether alkyl quaternary amine is present at a concentration from 0.01% to 20% by weight, calculated to the total concentration, and further wherein the composition is an aqueous conditioning composition comprising water.

2. The method according to claim 1 wherein the alkyl ether alkyl amine is stearoxypropyldimethyl amine present at a concentration from 0.01% to 1% by weight, calculated to the total concentration.

3. The method according to claim 1, wherein the arylated silicone is selected from the group consisting of phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane.

4. The method according to claim 1, wherein the at least one cationic polymer selected from the group consisting of Polyquaternium-6, Polyquaternium 10, Polyquaternium-11, silicone quaternium-18 and silicone quaternium-22.

* * * * *